Figure 1:
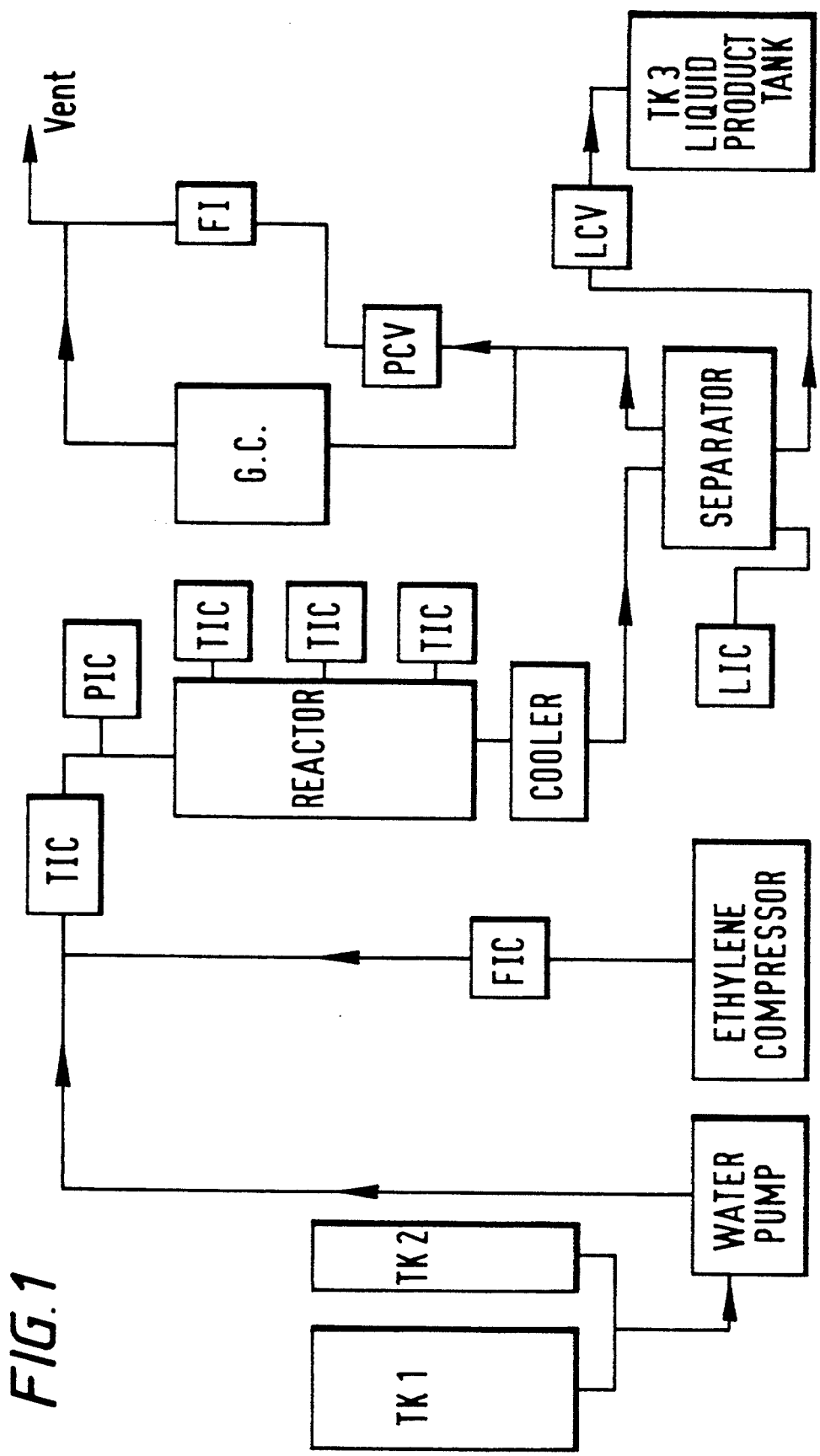

United States Patent [19]
Cockman et al.

[11] Patent Number: 5,349,096
[45] Date of Patent: Sep. 20, 1994

[54] OLEFIN HYDRATION PROCESS

[75] Inventors: Russell W. Cockman, Linlithgow; Gordon J. Haining; Philip Lusman, both of Stirlingshire; Archibald D. Melville, Falkirk, all of Scotland

[73] Assignee: BP Chemicals Limited, London, England

[21] Appl. No.: 88,799

[22] Filed: Jul. 8, 1993

[30] Foreign Application Priority Data

Jul. 10, 1992 [GB] United Kingdom ............ 9214688.5

[51] Int. Cl.$^5$ .................... C07C 29/04; C07C 31/08; C07C 31/10
[52] U.S. Cl. .................................................. 568/896
[58] Field of Search .......................................... 568/896

[56] References Cited

U.S. PATENT DOCUMENTS

| | | | |
|---|---|---|---|
| 3,917,721 | 11/1975 | Frampton ............................ | 568/896 |
| 3,953,533 | 4/1976 | Sommer et al. ...................... | 568/896 |
| 3,996,338 | 12/1976 | Frampton . | |
| 4,012,452 | 3/1977 | Frampton ............................ | 568/896 |
| 4,038,211 | 7/1977 | Frampton . | |
| 4,297,241 | 10/1981 | Kavasmaneck et al. ........... | 568/896 |
| 4,351,970 | 9/1982 | Sommer et al. ...................... | 568/896 |
| 4,371,456 | 2/1983 | Kadlec et al. ........................ | 568/896 |
| 4,808,559 | 2/1989 | Sommer et al. . | |
| 4,937,394 | 6/1990 | Dreibelbis ............................ | 568/896 |
| 5,086,031 | 2/1992 | Deller et al. . | |

FOREIGN PATENT DOCUMENTS

| | | |
|---|---|---|
| 844004 | 6/1970 | Canada . |
| 2237015 | 2/1973 | Fed. Rep. of Germany ...... 568/896 |
| 1306141 | 2/1973 | United Kingdom . |
| 1371905 | 10/1974 | United Kingdom . |
| 1476534 | 6/1977 | United Kingdom . |
| 1570650 | 7/1980 | United Kingdom . |

OTHER PUBLICATIONS

Huls Catalyst Data Sheet, Sep. 1988.
Degussa 350 Product Data Sheet, 1991.

*Primary Examiner*—Joseph E. Evans
*Attorney, Agent, or Firm*—Brooks Haidt Haffner & Delahunty

[57] ABSTRACT

This invention relates to a method for the hydration of olefins to the corresponding alcohols in the presence of a catalyst system comprising phosphoric acid catalyst supported on a siliceous support. One of the features of the invention is the use of a support which has a high crush strength, a high porosity and low metallic impurities. Using such a support, the catalyst system and the reaction conditions specified not only increase the life of the catalyst system by preventing loss of the crush strength of the support but also the improve the space-time-yield of the alcohol produced.

10 Claims, 1 Drawing Sheet

OLEFIN HYDRATION PROCESS

The present invention relates to a process for the hydration of olefins using a catalyst system comprising phosphoric acid supported on synthetic silica.

Hydration of olefins such as ethylene or propylene to the corresponding alcohols by hydration thereof in the vapour phase using a phosphoric acid catalyst deposited on a siliceous support is well known. Numerous prior art publications described such a procedure including those disclosed in GB-A-1570650, U.S. Pat. No. 4,808,559, GB-A1371905, U.S. Pat. No. 4,038,211, U.S. Pat. No. 4012452, GB-A-1476534, GB-A-1306141, U.S. Pat. No. 3,996,338 and CAN-A-844004. In each of these prior publications, the nature of the siliceous support used is defined by various parameters including the pore volume, the surface area, the crush strength and the purity of the support. However, none of these documents identify the precise combination of physical parameters of the support for maximising the performance of the supported catalyst. U.S. Pat. No. 5,086,031 on the other hand describes pressed parts of pyrogenically produced silicon dioxide of high crush strength and the use thereof as catalyst in the ethylene hydration method. However, this document does not disclose the use of such pressed parts as a support for a catalyst in a vapour phase process for the hydration of olefins under specific conditions.

It has now been found that by carefully controlling the aspects referred to above and especially by using supports of high porosity, purity and crush strength, it is possible to improve the performance of the catalyst system.

Accordingly, the present invention is a process for hydrating olefins to the corresponding alcohols in the presence of a catalyst system comprising phosphoric acid catalyst supported on a siliceous support characterised in that a. the mole ratio of water to olefin passing through the reactor is in the range from 0.15–0.50, b. the space velocity of the water/olefin mixture is from 0.010 to 0.100 g/min/cm$^3$ of the catalyst system, c. the phosphoric acid concentration is from 5 to 55% w/w based on the total weight of the catalyst system, d. the siliceous support is a silica having a porosity of at least 0.8 ml/g and an average crush strength of at least 5.5 Kg and having a purity of at least 99% w/w, e. the olefin hydration reaction is carried out at a temperature from 170°–300° C., and f. the reaction is carried out at a pressure ranging from 2000–24000 Kpa.

The olefins to be hydrated are suitably ethylene or propylene and the corresponding alcohols formed are suitably ethanol, n-propanol and isopropanol respectively. The process is carried out in the vapour phase, i.e. both the olefin and water are in the vapour phase over the catalyst system, apart from a small proportion of each gaseous reactant which dissolves in the catalyst system. The hydration reaction is believed to occur between such dissolved reactants. Ethers corresponding to the olefin are formed as by-products during the reaction.

The catalyst system used is phosphoric acid impregnated on a silica support. The silica support is suitably in the form of pellets or beads or are globular in shape having a particle diameter of 2 to 7 mm, preferably 4 to 6 mm. The silica support used has a porosity of at least 0.8 ml/g, suitably at least 0.85 ml/g preferably at least 0.9 ml/g. The catalyst has a crush strength of at least 5.5 Kg force, suitably at least 6 Kg force, preferably 7 Kg force and more preferably 7.5 Kg force. The crush strengths quoted are based on average of that determined for each set of 50 beads/globules on a CHATTILLON tester which measures the minimum force necessary to crush a particle between parallel plates. The bulk density of the support is suitably at least 380 g/l, preferably at least 440 g/l.

The support suitably has an average pore radius (prior to use) of 10 to 500 Angstroms, preferably an average pore radius of 30 to 100 Angstroms.

In order to achieve optimum performance, the silica support has at least 99% w/w purity, i.e. the impurities are less than 1% w/w, suitably less than 0.60% w/w and preferably less than 0.30% w/w.

The silica support used is most preferably a synthetic silica such as those produced by the so called "sol-gel" process or by the hydrolysis of SiCl$_4$. Specific examples of such synthetic silica supports include Support No. 350 made by pelletisation of Aerosil® 200 (ex Degussa).

The silica supports used herein have a great capacity to absorb phosphoric acid catalyst. The catalyst is suitably absorbed on the support by immersing the support in an aqueous solution of phosphoric acid. Where an aqueous solution of phosphoric acid is used, it suitably contains from 15 to 75% w/w of phosphoric acid, preferably from 30 to 55% w/w. The impregnated support is then dried before use to form the catalyst system and has a concentration of phosphoric acid ranging from 5 to 55% w/w, preferably from 20 to 48%w/w based on the total weight of the catalyst system.

The hydration reaction is carried out by placing the catalyst system in a reactor, sealing the reactor and then heating the catalyst system to the reaction temperature. The catalyst system is heated to a temperature from 170° to 300° C. depending upon the end product desired. For instance, if the end product is ethanol from ethylene, the catalyst system is suitably heated from 225° to 280° C., preferably from 230°–260° C., more preferably from 235°–245° C. On the other hand, if the end product is n-propanol or iso-propanol from propylene, the catalyst system is suitably heated from 180°–225° C., preferably from 185°–205° C. When the catalyst system has attained the desired temperature a charge of the olefin and water in the vapour state is passed through the reactor. The mole ratio of water to olefin passing through the reactor is in the range from 0.15 to 0.50, preferably from 0.25 to 0.45, more preferably from 0.30–0.40. The space velocity of water vapour/olefin mixture passing through the reactor is subject to slight variations depending upon whether the reactant olefin is ethylene or propylene. For instance, in the case of ethylene, the space velocity of the mixture thereof with water vapour is suitably from 0.010 to 0.100, preferably from 0.020 to 0.050 grammes per minute per cm$^3$ of the catalyst system. In the case of a mixture of propylene and water vapour, the space velocity is suitably in the from 0.010–0.100, preferably from 0.02–0.07 g/min/cm$^3$ of the catalyst system.

The hydration reaction is carried out at a pressure ranging from 2000 to 24000 Kpa. Within this range the hydration of ethylene is suitably carried out at a pressure from 3000 to 10000 KPa, whereas the hydration of propylene is suitably carried out at a pressure from 2000–7600 KPa.

The activity of the catalyst system was measured by monitoring the total amount of alcohol, ether and unreacted olefin produced over a one-hour period at standard test conditions (see Table on page 7 below), once a steady state had been reached in the pilot plant.

Alcohol and ether production was measured by gas chromatography using a Perkin Elmer Sigma 4B GC (see below), whereas unreacted olefin was metered using a wet-type positive displacement flow meter (ex Alex Wright & Co, Model DM3F).

A very important and unexpected feature of the present invention which distinguishes it over the conventional catalyst systems for hydration of olefins is that the siliceous support used retains its relatively high initial crush strength even after prolonged use which extends to the total life of the catalyst system. In fact, in some instances (see e.g. Table 1 below), the crush strength of the support has been shown to increase after use rather than decrease as is the case, and as would be expected, with all conventional supports of the silica gel type used hitherto. This is the case even when the initial crush strength of the conventional supports is the same as or greater than the supports now used. In the current set of olefin hydration tests carried out with the catalyst systems now claimed, no change in the crush strength was noted even after the catalyst system had been on stream for over 1500-2000 hours. In contrast, most conventional silica gel based systems begin to lose their crush strength after about 500-700 hours on stream thereby reducing the life of the support used and hence the catalyst system has to be replaced frequently. In the catalyst system now used, any loss of activity is due to deposition of carbon on the siliceous support without any loss of its crush strength.

Thus, it has now been found that by using the specific support described herein it is possible not only to increase the space-time-yield (hereafter "STY") of the process but also to prolong the life of the support thereby reducing the frequency with which the support is changed or replaced on a plant.

The present invention is further illustrated with reference to the following Examples:

EXAMPLE 1

Production of Ethanol

This was a pilot plant experiment (represented by the enclosed schematic FIG. 1) and the following procedure was used:

A 0.30:1 molar mixture of water and ethylene (6895 KPa, (1000 psig) 240° C.) was passed down through a 5.08 cm I D copper lined stainless steel reactor containing 1000 cc zone of hydration catalyst system. Water was fed to the reactor by a diaphragm metering pump from a small calibrated glass tank (TK2 in FIG. 1), whereas the ethylene (>99.9% v/v) was fed to the reactor by a compressor operating at 6998.4 KPa (1015 psig). The inlet flow of ethylene to the pilot plant was measured using an orifice plate and was controlled using a pneumatic flow control valve. Both streams passed through an electrically heated feed vaporiser prior to entering the reactor. The temperature in the reactor was measured by four radial thermocouples spaced equidistantly in the zone containing the catalyst system, and the reactor wall heaters were set to give a 20° C. temperature gradient across the reactor. This imposed exotherm was used to simulate an adiabatic commercial process.

The effluent from the reactor was then passed through a cooler into a high pressure separator. These two units were kept at 100° C. by steam tracing. A mixture of hot gases (ethylene, ethanol and diethylether) was then removed from the top of the separator through a pressure control valve to a vent and metering system. A small bleed was then taken to a GC sampling system. The remaining liquid phase in the separator (water, ethanol and a trace of ether) was taken off by a valve controlled by the separator's liquid level, and was collected in TK3 (see FIG. 1).

For a test period, the liquid product was collected over one hour during which time the gas phase concentrations of ethanol and diethylether were automatically measured by GC every 15 minutes (see below). At the end of the test period the liquid product was collected from TK3 (see FIG. 1), made up to a standard volume, and then analysed by GC. The total amount of ethanol and diethylether produced in one hour is simply the sum of the amounts found in the liquid and gas phases.

The GC analyses referred to above for ethanol and diethylether were carried out on a Perkin Elmer Sigma 4B GC, operated at 90° C. The GC columns used were of 4 m×2 mm ID stainless steel, packed with 20% polyethylene glycol 1540 on Chromosorb ® W (60-85 BS mesh), with separate columns being used for gas and liquid analyses. Gas samples were analysed automatically every 15 minutes under computer control, whereas liquid samples were collected and then manually injected into the GC using tert-butyl alcohol as an internal standard. In both cases the resulting chromatographs were then integrated by computer and the concentrations of ethanol and diethylether present in each sample was calculated.

The standard test conditions used during pilot plant evaluation of the catalyst systems of the present invention are tabulated below. These conditions were such that the pilot plant simulated precisely the conditions typically used by commercial units to achieve a maximum production rate.

| STANDARD TEST CONDITIONS | |
|---|---|
| PROCESS VARIABLE | CONDITIONS |
| Reactor Pressure | 6895 KPa (1000 psig) |
| Reactor Inlet Temperature (°C.) | 240 |
| Reactor Exit Temperature (°C.) | 260 |
| Ethylene Space Velocity | 1442 g/l cat/hr |
| Water Space Velocity | 280 g/l cat/hr |
| Water:Ethylene Mole Ratio | 0.30 |
| $H_3PO_4$:Loading on support | 300 g/l |
| Silica Support Used | Degussa 350 (Pelletised Aerosil ® 200) |

The supports and catalysts of the catalyst systems of the present invention used in this Example had the following physical characteristics:

| CHARACTERISTICS | DEGUSSA 350 |
|---|---|
| Pore vol ml/g | 0.82 |
| ml/l cat vol | 400 |
| Bulk Density g/l | 488 |
| Crush strength Kg | |
| Fresh support | 7 |
| Fresh Catalyst System | 8.5 |
| Used Catalyst System | 15 |
| Attrition % w/w | |
| Fresh support | — |
| Fresh Catalyst System | <1% |
| Mean Pore radius Fresh | 77 |

| CHARACTERISTICS | DEGUSSA 350 |
| --- | --- |
| support (Angstroms) Mean Pore Radius Fresh Catalyst System (Angstroms) | 79 |

The effect of the specific supports now used in the catalyst systems for the hydration of olefins under the standard conditions shown above on the space-time-yield (STY) of ethanol are:

TABLE 1

| DEGUSSA 350 | Fresh Support | Catalyst System No. 1 | Catalyst System No. 2 |
| --- | --- | --- | --- |
| Acid Loading (g/l) | — | 362 | 308 |
| Bulk Density (g/l) | 488.3 | 851 | 796 |
| Pore Volume ($H_2O$, ml/g) | 0.83 | 0.87 (unused) 0.81 (used) | 0.86 (unused) 0.78 (used) |
| Attrition (% w/w) | 0.30 | 0.12 | 0.75 |
| Crush strength (Kg) | 7.2 | 8.8 (unused) 9.4 (used- 3 days) | 7.9 (unused) 15.1 (used- 15 days) |
| Ethanol STY (G/L/H) | — | 108 | 102 |

The above results show that the use of a support of relatively high crush strength and superior pore volume gives rise to a higher space-time-yield of ethanol than the conventional catalyst systems based on silica gel supports for olefin hydration under comparable process conditions.

Using the same method as in the process described above but by varying the reaction conditions as shown under 'NOTES' under each Table to test the effect of water:ethylene mole ratios (see Table 2 below), the effect of relative flow rates (see Table 3 below), the effect of reaction pressure (see Table 4 below) and the effect of reaction temperature on the yield of the alcohol, the following results were obtained.

TABLE 2

EFFECT OF WATER:ETHYLENE MOLE RATIO ON OLEFIN HYDRATION REACTION

| $H_2O:C_2H_4$ Mole Ratio | Ethanol STY (G/L/H) | Ether STY (G/L/H) | Ethylene Conversion | Av. Reactor Temp °C. |
| --- | --- | --- | --- | --- |
| 0.300 | 110.6 | 112.8 | 10.63% | 250.4 |
| 0.352 | 113.0 | 86.2 | 9.33% | 249.9 |
| 0.400 | 111.2 | 62.9 | 8.13% | 250.1 |

NOTES:
1) Phosphoric acid loading in catalyst system = 306 G/L
2) Reactor pressure = 6895 KPa (1000 psig)
3) Inlet ethylene flow = 1.44 kg/h
4) Mole ratio changed by altering water feed rate

TABLE 3

EFFECT OF RELATIVE FLOW RATE ON OLEFIN HYDRATION REACTION

| Relative Flow Rate | Ethanol STY (G/L/H) | Ether STY (G/L/H) | Ethylene Conversion | Av. Reactor Temp °C. |
| --- | --- | --- | --- | --- |
| 100.0% | 113.0 | 108.7 | 10.34% | 250.2 |
| 140.5% | 143.4 | 102.8 | 8.15% | 250.2 |

NOTES:
1) Phosphoric acid loading in catalyst system = 306 G/L
2) Reactor pressure = 6895 KPa (1000 psig)
3) 100% relative flows = standard test conditons

TABLE 4

EFFECT OF PROCESS PRESSURE ON OLEFLIN HYDRATION REACTION

| Process Pressure | Ethanol STY (G/L/H) | Ether STY (G/L/H) | Ethylene Conversion | Av. Reactor Temp °C. |
| --- | --- | --- | --- | --- |
| 6895 KPa | 108.8 | 102.7 | 10.08% | 250.4 |
| 6205.5 KPa | 105.6 | 98.6 | 9.66% | 250.6 |
| 5516 KPa | 100.7 | 91.6 | 9.17% | 250.5 |

NOTES:
1) Phosphoric acid loading in catalyst system = 306 G/L
2) All other variables at standard test conditions

TABLE 5

EFFECT OF PROCESS TEMPERATURE ON OLEFIN HYDRATION REACTION

| Reactor Inlet Temp (°C.) | Reactor Exit Temp (°C.) | Ethanol STY (G/L/H) | Ether STY (G/L/H) | Ethylene Conversion |
| --- | --- | --- | --- | --- |
| 245 | 265 | 109.4 | 107.2 | 10.44% |
| 240 | 260 | 105.4 | 98.0 | 9.66% |
| 235 | 255 | 98.7 | 71.1 | 7.88% |

NOTES:
1) Phosphoric acid loading in catalyst system = 306 G/L
2) All other variables at standard test conditions
3) Data taken after 45 days on stream; initial crush strength unchanged after being on stream for 72 days (1728 hrs)

EXAMPLE 2

Production of n-Propanol & Iso-propanol

Description of Equipment

All experiments to measure the performance of a catalyst system based on Degussa 350 pelletised silica support for hydrating propylene to isopropanol were carried out in a small copper lined tubular reactor containing 50 ml of the catalyst system. Water and propylene (>99% vol/vol) were fed to this reactor by metering pumps, and passed through a preheater/vapouriser prior to entering the supported catalyst zone.

The reactor was isothermally heated using a fluidised bath, the temperature of which was controlled to within ±0.5° C. The pressure of the process was measured at the inlet of the reactor, and was controlled to within ±6.9 KPa (1 psig).

The gaseous product stream exiting the reactor was then dropped in pressure to about ambient, condensed and degassed. The offgas was then thoroughly scrubbed with water to remove any residual alcohol, and the gas (mainly unreacted propylene) was then accurately metered prior to being vented.

The activity of each catalyst system was assessed by collecting the condensed product, plus all the scrubbing water, over a 10 hour test period, and then analysing each stream for isopropanol and n-propanol content. The total production of each alcohol is simply the sum of the alcohol found in the condensate and the scrubbing water.

Catalyst Systems Tested

Three catalyst systems were tested on the above equipment to demonstrate the superiority of those supported on synthetic silicas over those supported on conventional montmorillonite:

(a) A catalyst system in which phosphoric acid is supported on fresh montmorillonite and containing an acid loading of 160 g/l (ex Huels).

(b) A catalyst system in which phosphoric acid is supported on montmorillonite(ex Huels) which has been re-soaked in fresh orthophosphoric acid to give an acid loading of 180 g/l.

(c) A catalyst system made by absorbing orthophosphoric acid onto pelletised silica (Degussa 350), to give an acid loading of 181 g/l.

All catalyst systems were tested at a reactor inlet pressure of 3896 KPa (565 psig), at temperatures ranging from 185° to 200° C., and at a water:olefin feed mole ratio of 0.30.

Results (A) ISOPROPANOL PRODUCTION FROM MONTMORILLONITE AND SYNTHETIC SILICA SUPPORTED CATALYSTS

| Reaction Temp. (°C.) | Fresh Commercial Catalyst System STY (G/L/H) | Resoaked Commercial Catalyst System STY (G/L/H) | Catalyst System of Invention STY (G/L/H) |
|---|---|---|---|
| 185 | — | 191.5 | 238.6 |
| 190 | 176.3 | 195.4 | 227.0 |
| 195 | 168.0 | — | — |
| 200 | 179.5 | 190.9 | 208.5 |

(B) N-Propanol Production from Montmorillonite and Synthetic Silica Supported Catalysts

| Reaction Temp. (°C.) | Fresh Commercial Catalyst System STY (G/L/H) | Resoaked Commercial Catalyst System STY (G/L/H) | Catalyst System of Invention STY (G/L/H) |
|---|---|---|---|
| 185 | — | 0.356 | 0.640 |
| 190 | 0.310 | 0.496 | 0.947 |
| 195 | 0.525 | — | — |
| 200 | 0.845 | 1.506 | 2.194 |

The results clearly show that olefin hydration catalysts supported on synthetic silicas according to the present invention are significantly more active for both isopropanol and n-propanol production than those supported on montmorillonite.

We claim:

1. A method of hydrating olefins to the corresponding alcohols in the presence of a phosphoric acid catalyst supported on a siliceous support characterized in that (a) the mole ratio of water to olefin passing through the reactor is in the range from 0.15-0.50, (b) the space velocity of the water/olefin mixture is from 0.010 to 0.100 g/min/cm$^3$ of the catalyst system, (c) the phosphoric acid concentration is from 5 to 55% w/w based on the total weight of the catalyst system, (d) the said siliceous support is derived from a non-porous silica and the siliceous support has a porosity of at least 0.8 ml/g and an average crush strength of at least 5.5 Kg and has a purity of at least 99% w/w, (e) the olefin hydration reaction is carried out at a temperature from 170°-300° C., and (f) the said reaction is carried out at a pressure from 2000-24,000 Kpa.

2. A method according to claim 1 wherein the mole ratio of olefin to water passing through the reactor is in the rage from 0.25-0.45.

3. A method according to claim 1 wherein the space velocity of water/olefin mixture when the olefin is ethylene is in the range from 0.020-0.050 g/min/cm$^3$ of the catalyst system.

4. A method according to claim 1 wherein the space velocity of water/olefin mixture when the olefin is propylene is in the range from 0.020-0.070 g/min/cm$^3$ of the catalyst system.

5. A method according to claim 1 wherein the phosphoric acid concentration is 20-48% w/w based on the total weight of the catalyst system.

6. A method according to claim 1 wherein the siliceous support has a porosity of at least 0.85 ml/g.

7. A method according to claim 1 wherein the siliceous support has an average crush strength of at least 7 Kg force.

8. A method according to claim 1 wherein the siliceous support has impurities of less than 0.60% w/w.

9. A method according to claim 1 wherein the catalyst system is heated to a temperature from 225°-280° C. for the hydration of ethylene to ethanol and from 180°-225° C. for the hydration of propylene to isopropanol.

10. A method according to claim 1 wherein the olefin hydration reaction is carried out at a pressure from 3000 to 10000 Kpa when the olefin is ethylene and from 2000-7600 KPa when the olefin is propylene.

* * * * *

UNITED STATES PATENT AND TRADEMARK OFFICE
CERTIFICATE OF CORRECTION

PATENT NO. : 5,349,096
DATED : September 20, 1994
INVENTOR(S) : Russell W. Cockman, et al It is certified that error appears in the above-indentified patent and that said Letters Patent is hereby corrected as shown below:

Column 8, line 10, correct the spelling of "range".

Signed and Sealed this

Fourteenth Day of March, 1995

Attest:

BRUCE LEHMAN

Attesting Officer

Commissioner of Patents and Trademarks